United States Patent [19]

Young

[11] 4,024,431

[45] May 17, 1977

[54] RESONANCE METAL ATOM LAMP

[75] Inventor: Robert A. Young, Loretto, Canada

[73] Assignee: Xonics, Inc., Van Nuys, Calif.

[22] Filed: June 23, 1975

[21] Appl. No.: 589,699

[52] U.S. Cl. .................................. 315/248; 313/15; 313/180; 313/225; 313/185

[51] Int. Cl.² ........................................ H05B 41/24

[58] Field of Search ............ 313/225, 110, 15, 180, 313/201, 220, 209; 315/267, 344, 248

[56] References Cited
UNITED STATES PATENTS

| | | | |
|---|---|---|---|
| 3,851,214 | 11/1974 | Young | 313/220 X |
| 3,898,501 | 8/1975 | Hosoya et al. | 313/209 X |

*Primary Examiner*—R. V. Rolinec
*Assistant Examiner*—Darwin R. Hostetter
*Attorney, Agent, or Firm*—Harris, Kern, Wallen & Tinsley

[57] ABSTRACT

A controllable evaporation source of parent metal species, produced either from a volatile metal or a metal halide, and under some circumstances a chemical getter sink in a sealed RF excited discharge. This discharge occurs in a second, extremely pure gas which is present in great excess over the gas produced by evaporization which may be followed by chemical decomposition. Excitation of species whose emission is desired occurs by electron impact or energy transfer from the major species which are in turn, excited by the electron impact.

16 Claims, 2 Drawing Figures

RESONANCE METAL ATOM LAMP

The present invention relates generally to the emission and detection of atomic spectral lines and more specifically to the detection of the atomic resonance lines of a wide range of metals.

It is well known that, if radiation from an atomic spectral light source characteristic of a given element or elements is allowed to fall on an atomic vapor of the same element or elements, selected lines in the spectrum emitted by the light source will be partially absorbed by the atomic vapor. For the purposes of this specification such lines will be referred to an atomic resonance lines. It is further known that, if the atomic vapor is under the right physical conditions, i.e. pressure, etc., some of the radiation which is absorbed by the atomic vapor will be re-emitted in all directions.

It is an object of this invention to measure the concentration of metal atoms by measuring the intensity of the scattered resonance radiation of the metal atoms.

A further object of this invention is to create a source of atomic resonance radiation characteristic of metals by the use of a low power sealed resonance lamp.

These and other objects of the invention will become apparent from the following description when taken in conjunction with the drawings wherein.

Broadly speaking, the present invention utilizes a controllable evaporation source of parent metal species, produced either from a volatile metal or a metal halide, and under some circumstances a chemical getter sink in a sealed RF excited discharge. This discharge occurs in a second, extremely pure gas which is present in great excess over the gas produced by evaporization which may be followed by chemical decomposition. Excitation of species whose emission is desired occurs by electron impact or energy transfer from the major species which are in turn, excited by the electron impact.

A low power resonance lamp used with a source of diatomic gas is described in U.S. Pat. No. 3,851,214 issued in the name of the present inventor.

Figure 1:
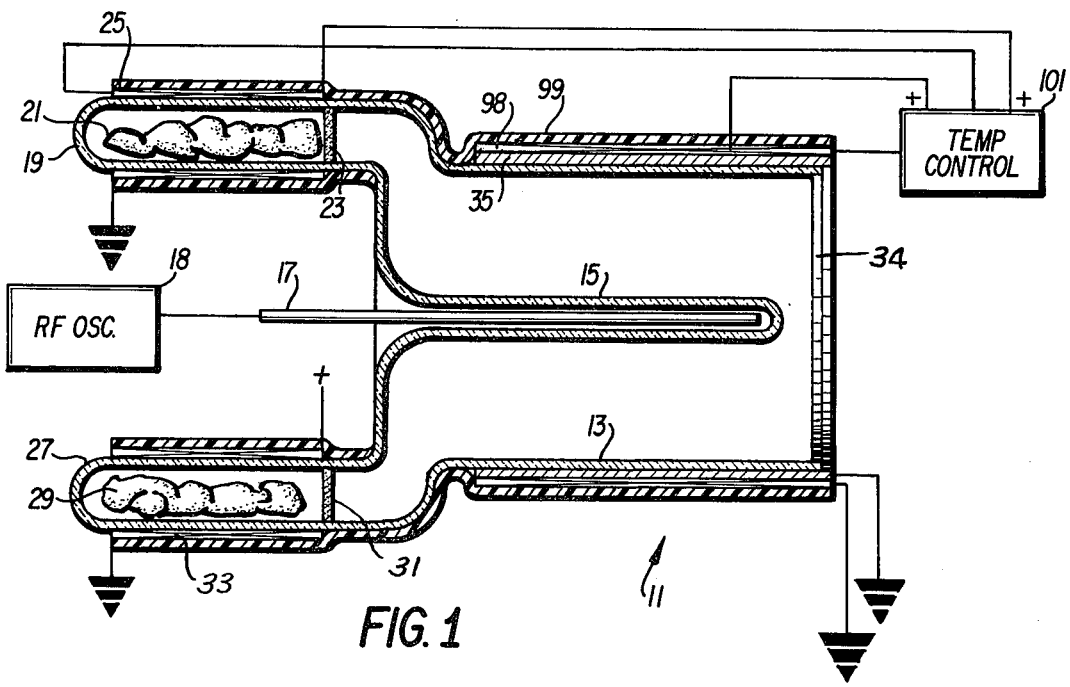
FIG. 1 is a schematic diagram of the tube of the present invention.
Figure 2:
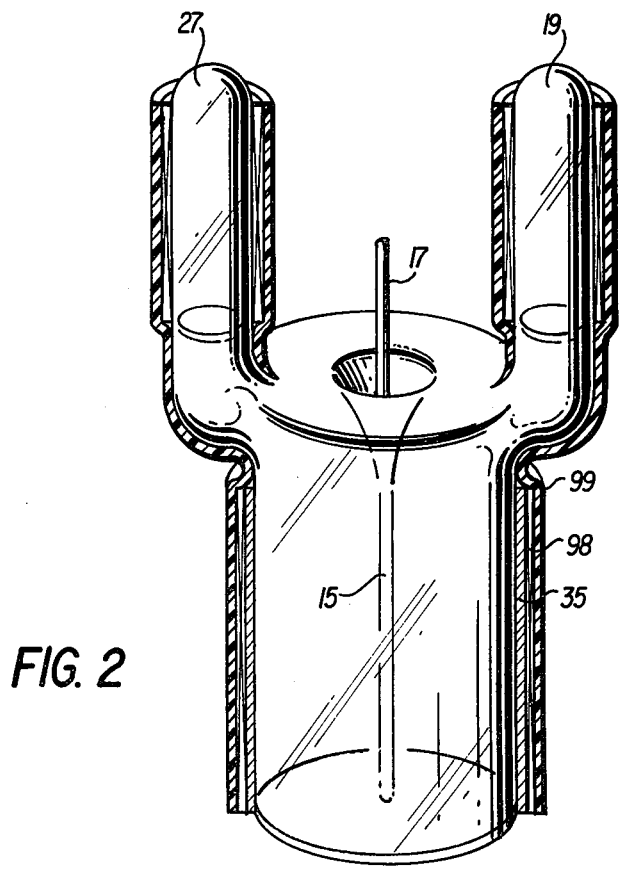
FIG. 2 is a perspective view of a preferred embodiment of the present invention.

Illustrated in FIG. 1 is a cylindrical body 11 having a glass wall 13 and a hollow reentrant element 15. Reentrant element 15 extends coaxially substantially the length of the cylinder. An electrical conductor 17 is contained within the hollow reentrant element and extends outwardly to connect to an RF energy source 18.

A first hollow arm 19 is integral with cylinder 13 and extends outwardly therefrom. The arm is closed at the outer end and is filled with a greater or scavenger 21 such as uranium or a barium, or some other metal. A gas permeable barrier 23, such as glass frit, in hollow arm 19 prevents the getter from moving into the cylinder. Heating means 25 here illustrated as an electrical heater is provided about the arm so as to heat the getter material if necessary.

A second arm 27 also extends from the cylinder and is closed at its outer end. This arm contains the source 29 of the species which, when added to the discharge produces the desired emission. A barrier 31 and a heater 33 are also provided on arm 27.

Cylindrical body 13 is closed at the other end by a window 34 which is transparent to the spectral emission of the species being examined. A special cement may be required to attach the window to the body of the lamp, although the window may be of the same material as the lamp body.

In order to complete the necessary path for electrical excitation, the outside of cylinder 13 may be coated with an electrically conductive material 35 and this coating is grounded as shown. If the cylinder is largely contained within a close fitting grounded conducting enclosure, a separate coating is not required. In either case the cylinder is effectively sheathed by a conductive element.

The body 11 of the lamp may be heated by a heater 98 adjacent but electrically insulated from electrically conductive material 35. One such heating means is a standard electrical heating cable. In order to retain the heat, a heat insulating material 99 may be placed about heater 98.

In order to maintain the main body 13 of the lamp at a temperature higher than that of arm 19 and 27, a temperature control may be used. Temperature control 101 is shown schematically and includes the power supply as indicated. The temperature sensing connections are shown by the unmarked lines. It is necessary to maintain this temperature differential to prevent deposition on the inside of the main body 13 and on the window.

The lamp of the present invention may be used to produce emission of a number of desired species. Examples of such use are shown below.

The lamp of the present invention provides a means for detecting and measuring the concentrations of both volatile and non-volatile metals.

Examples of such volatile metals are Hg, Cs, Cd, I, K, Na, Rb. These lamps use the pure element and the temperature of the side-arm is adjusted to give the desired emission characteristics. The lamp body is heated hotter than the source arm to prevent condensation of the elements in the discharge region. The inner wall of the tube is made passive to prevent interaction of the element with the glass. The getter could be a barium containing compound and the frit be adjusted in porosity to prevent significant source element material from reaching the getter whose function in this application is to maintain the purity of the filler gas. The filler gas is He, Ar, Kr, Xe, or Ne at a pressure near one torr.

Example of non-volatile metals are Ag, Al, As, Au, Ba, Be, Bi, Ca, Co, Cr, Cu, Fe, Ga, Ge, Hf, In, Mn, Mo, Pd, Sb, Sc, Se, Si, Sn, Sr, Te, Tl, Ti, U, Va, Zn.

In these lamps, the source compound is either the chloride or iodide of the desired metal. The lamp body is again heated hotter than the source compound by heater 98 to prevent the metal halide from condensing. The temperature in these applications usually requires that the lamp be constructed of quartz, or other similar material. The getter side-arm again contains a material such as a barium containing compound (decomposed $BaN_3$, for example) mainly to keep the filler gas, Ar, Ne, Kr, Xe, pure. Because the getter may remove $Cl_2$ or $I_2$, and this may be undesirable under some circumstances, since the metal is removed from the discharge tube surfaces by reactions with $Cl_2$ or Cl, $I_2$, or I, it may be necessary to replace the getter in the side-arm by a thermal decomposition source of $Cl_2$, such as $AuCl_3$, or or a thermal decomposition source of $I_2$. In this case, the source arm containing the metal chloride or iodide will also contain some of the pure metal to act as a getter of free $Cl_2$ or $I_2$.

The above description and accompanying drawings are illustrative only since geometric configurations and components could be varied without departing from the invention. Accordingly the scope of the invention is to be limited only by the following claims.

I claim:
1. A resonance lamp comprising
a dielectric closed body having a predetermined vacuum therein;
a reentrant coaxial hollow glass element integral within said body and extending from one end thereof substantially the length of said body;
an electrical conductor within said element;
an ultraviolet transparent window at the other end of said body;
two hollow arms integral with and extending from said body;
a high purity rare gas filling within said body at a pressure of 1 to 10 torr;
a source of metal atoms in one of said arms;
an electrically conductive sheathing adjacent said glass body;
a getter in the other said arm for removing gases from said body;
a means for heating the main body of said housing; and
means for heating said one arm, with the temperature in said main body higher than the temperature in said one arm.
2. The resonance lamp of claim 1 wherein said getter is in the form of a Ba containing compound.
3. The resonance lamp of claim 1 wherein said metal atoms are Cs produced by evaporation of Cs.
4. The resonance lamp of claim 1 wherein the getter is uranium.
5. The resonance lamp of claim 1 further comprising
a source of RF power connected to said electrical conductor; and
means for grounding said sheathing adjacent the exterior of said body.
6. A resonance lamp comprising
a closed housing;
a hollow reentrant element at one end of said housing and extending coaxially with said housing substantially the entire length thereof;
an electrical conductor within said hollow reentrant element and extending outwardly thereof;
an ultraviolet transparent window at the other end of said housing;
an electrically conductive sheathing adjacent the exterior of said housing;
a first hollow arm integral with and extending from said housing;
a second hollow arm integral with and extending from said housing;
a source of metal halide within said first arm;
a getter in said second arm;
an inert gas in said cylindrical housing; and
a means for heating the main body of the closed housing to a temperature above the temperature of said first arm.
7. The resonance lamp of claim 6 wherein said inert gas is helium.
8. The resonance lamp of claim 6 wherein said getter is replaced by a thermal decomposition source of $Cl_2$.
9. The resonance lamp of claim 6 wherein said getter is replaced by a thermal decomposition source of $I_2$.
10. The resonance lamp of claim 6 wherein said inert gas is Argon.
11. The resonance lamp of claim 8 wherein said thermal decomposition source produces $Cl_2$; and
further comprising a means for heating said arms.
12. The resonance lamp of claim 9 wherein said thermal decomposition source produces $I_2$; and
further comprising means for heating said arms.
13. The resonance lamp of claim 6 wherein said source of metal halide is a metal chloride and further comprising;
means for heating said first arm.
14. The resonance lamp of claim 6 wherein said source of metal halide is a metal iodide and further comprising;
means for heating said source.
15. The resonance lamp of claim 1 wherein said source of metal atoms is a pure volatile metal.
16. The resonance lamp of claim 1 wherein said source of metal atoms is a metal halide.

* * * * *